US009562910B2

(12) United States Patent
Dunweber et al.

(10) Patent No.: US 9,562,910 B2
(45) Date of Patent: *Feb. 7, 2017

(54) METHOD FOR PRODUCING ACYLATED PEPTIDES

(75) Inventors: Dorte Lunoe Dunweber, Virum (DK); Inge Holm Jensen, Smorum (DK); Louis Brammer Hansen, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 13 days.

This patent is subject to a terminal disclaimer.

(21) Appl. No.: 12/651,782

(22) Filed: Jan. 4, 2010

(65) Prior Publication Data
US 2010/0105863 A1    Apr. 29, 2010

Related U.S. Application Data

(63) Continuation of application No. 11/843,182, filed on Aug. 22, 2007, now abandoned, which is a continuation of application No. 10/671,260, filed on Sep. 25, 2003, now Pat. No. 7,273,921.

(60) Provisional application No. 60/413,684, filed on Sep. 26, 2002.

(30) Foreign Application Priority Data

Sep. 25, 2002 (DK) .................................. 2002 01421

(51) Int. Cl.
*A61K 38/00* (2006.01)
*G01N 33/68* (2006.01)
*C07K 1/00* (2006.01)
*C07K 1/107* (2006.01)
*C07K 14/575* (2006.01)
*C07K 14/605* (2006.01)
*C07K 14/62* (2006.01)

(52) U.S. Cl.
CPC .......... *G01N 33/6842* (2013.01); *C07K 1/006* (2013.01); *C07K 1/1077* (2013.01); *C07K 14/57563* (2013.01); *C07K 14/605* (2013.01); *C07K 14/62* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 3,950,517 A | 4/1976 | Lindsay et al. | |
| 4,126,628 A * | 11/1978 | Paquet ............................ | 554/59 |
| 4,497,729 A | 2/1985 | Kitaura et al. | |
| 4,619,915 A | 10/1986 | Ives | |
| 5,104,651 A * | 4/1992 | Boone et al. ................. | 424/85.1 |
| 5,216,125 A | 6/1993 | Kouge | |
| 5,468,843 A | 11/1995 | Boyd et al. | |
| 5,512,549 A | 4/1996 | Chen et al. | |
| 5,905,140 A | 5/1999 | Hansen | |
| 5,986,050 A | 11/1999 | Shalaby et al. | |
| 6,451,974 B1 * | 9/2002 | Hansen ......................... | 530/345 |
| 6,720,304 B1 | 4/2004 | Sinn et al. | |
| 7,273,921 B2 * | 9/2007 | Dunweber et al. ........... | 530/345 |

FOREIGN PATENT DOCUMENTS

| | | |
|---|---|---|
| EP | 0011283 | 5/1980 |
| EP | 511600 A2 | 11/1992 |
| EP | 712862 A2 | 5/1996 |
| EP | 1227 107 | 7/2002 |
| JP | 55085552 | 6/1980 |
| JP | 55085552 A | 6/1980 |
| JP | 57114556 | 7/1982 |
| JP | 59148745 | 8/1984 |
| JP | 59148745 A | 8/1984 |
| JP | 06-256225 A | 2/1994 |
| JP | 11-502204 A | 2/1999 |
| JP | 4949557 B2 | 6/2012 |
| JP | 05-065275 B2 | 10/2012 |
| WO | 91/11457 A1 | 8/1991 |
| WO | WO 95/07931 | 3/1995 |
| WO | WO 98/02460 | 1/1998 |
| WO | 98/08871 | 3/1998 |
| WO | 98/08873 A1 | 3/1998 |
| WO | WO 98/08871 | 3/1998 |
| WO | WO 98/08872 | 3/1998 |
| WO | 98/51349 A1 | 11/1998 |
| WO | WO 98/51349 | 11/1998 |
| WO | 99/43708 | 9/1999 |
| WO | WO 99/43708 | 9/1999 |
| WO | WO 00/55119 | 9/2000 |
| WO | WO 0055119 A1 * | 9/2000 |
| WO | WO 01/04156 | 1/2001 |

OTHER PUBLICATIONS

Zuvanovic et. al. Biomedical Chromatography, vol. 14, pp. 56-57, 2000).*
Zivanovic et al. Biomedical Chromatography, vol. 14, pp. 56-57, 2000.*
Biomedical Chromatography, vol. 14, pp. 56-57, 2000.*
Zivanovic et. al. Biomedical Chromatography, vol. 14, pp. 56-57, 2000.*
Chuang-Wei, Ind. Eng. Chem. Res. 2006, 45, 791-795.*
James, Master Organic Chemistry, http://www.masterorganicchemistry.com/2012/04/27/polar-protic-polar-aprotic-nonpolar-all-about-solvents/, last visited Mar. 7, 2010*
The Unifac Consortium, Dielectric Constant of N-Methyl-2-pyrrolidone, http://www.ddbst.com/en/EED/PCP/DEC_C284.php. last visited Mar. 7, 2010.*
Non-Final Office Action dated May 23, 2001 in U.S. Appl. No. 09/523,783, filed Mar. 13, 2000 by Hansen.
Notice of Allowance dated Mar. 26, 2002 in U.S. Appl. No. 09/523,783, filed Mar. 13, 2000 by Hansen.
Riordan, J.F. et al., "Methods in Enzymology," Enzyme Structure, vol. 25, pp. 494-499 (1972).
Meguro, K. et al., Chem Pharm Bull., vol. 34(7), pp. 2840-2851 (1986).
International Search Report for WO 2004/029077, dated Mar. 1, 2004.

(Continued)

*Primary Examiner* — Jeanette Lieb
(74) *Attorney, Agent, or Firm* — Rosemarie R. Wilk-Orescan

(57) ABSTRACT

The present invention provides a method for acylating one or more amino groups of a peptide where the acylation reaction is to be performed in an aqueous mixture containing less than 10% w/w aprotic polar solvent.

25 Claims, No Drawings

(56) References Cited

OTHER PUBLICATIONS

Zivanovic et al., Biomedical Chromatography, vol. 14, pp. 56-57 (2000).
Miroshnikov, A. Mass Spectometic Determination. 1970 vol. 40(2) pp. 429-443.
Meguro et al., "Studies on Antidiabetic Agents. VII. Synthesis and Hypoglycemic Activity of 4-Oxazoleacetic Acid Derivatives", Chem. Pharm. Bull., 1986, vol. 34, No. 7, pp. 2840-2851.

* cited by examiner

METHOD FOR PRODUCING ACYLATED PEPTIDES

CROSS REFERENCE TO RELATED APPLICATIONS

This application is a continuation of U.S. application Ser. No. 11/843,182, filed Aug. 22, 2007, which is a continuation of U.S. application Ser. No. 10/671,260, filed Sep. 25, 2003, which claimed priority under 35 U.S.C. 119 of Danish application no. PA 2002 01421, filed Sep. 25, 2002, and U.S. provisional application No. 60/413,684, filed Sep. 26, 2002, the contents of which are fully incorporated herein by reference.

FIELD OF THE INVENTION

The present invention relates to methods for acylating peptides and proteins. More specifically, the invention relates to a method of introducing one or more acyl groups into a peptide or a protein.

BACKGROUND OF THE INVENTION

A large number of peptides have been approved for use in medical practice, and the peptides may be produced in suitable host cells by recombinant DNA technology or they may be produced synthetically by well established peptide synthesis technology. However, native peptides as well as analogues thereof tend to exhibit high clearance rates which are unacceptable for many clinical indication where a high plasma concentration of the peptide is required over a prolonged period of time. Examples of peptides which in their native form have a high clearance are: ACTH, corticotropin-releasing factor, angiotensin, calcitonin, insulin, glucagon, glucagon-like peptide-1 (GLP-1), glucagon-like peptide-2 (GLP-2), insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opioids and analogues thereof, superoxide dismutase, interferon, asparaginase, arginase, arginine deaminase, adenosine deaminase and ribonuclease.

A variety of derivatizations of peptides and peptide analogs have been found to influence the clearance rate of the peptides in a favourable direction. One such derivatization is the introduction of a lipophilic acyl group into the therapeutic peptide causing a desirable protracted profile of action relative to the non-acylated peptide. Hence, less frequent administration of the therapeutic protein improves the patients compliance to the prescribed therapy, and it reduces the amount of peptide to be administered. This has been described and demonstrated in WO98/08871, which i.a. discloses acylation of GLP-1 and analogs thereof, in WO98/08872, which i.a. discloses acylation of GLP-2 and analogs thereof, and WO99/43708, which i.a. discloses acylation of exendin and analogs thereof. Mono- or dipeptide spacers such as aspartic acid and glutamic acid, between the peptide and the acyl-group was demonstrated to be desirable. Spacers including a free carboxylic acid group must be protected before acylation and subsequently deprotected.

EP 1227107 discloses the acylation of ∈-amino groups of human insulin.

WO00/55119 discloses a method for acylating peptides (e.g. GLP-1) and novel acylating agents.

In order for therapeutic peptides to be economically viable the cost of producing the peptides as well as the therapeutic dosage of the peptide are pivotal. A major cost during production of therapeutic peptides is the purification steps required to separate the target protein from impurities which are closely related to the target protein, e.g. isomers, desamido forms etc. These purification steps are usually performed by chromatography implying expensive chromatography matrices and solvents as well as reduced overall yield.

It is the aim of the present invention to provide an efficient and economic method for the introduction of lipophilic groups into peptides via α-amino-α,ω-dicarboxylic acid spacers. The method is more specific, and thus results in higher yields and reduced formation of closely related impurities. A significant reduction of the cost of producing the acylated peptides are achieved. Less expensive acylated peptides are highly desirable for maximizing the number of patients for whom the treatment is available as well as for exploiting the advantages of alternative delivery routes which have lower bioavailability than subcutaneous injection, e.g. transdermal and pulmonal delivery.

SUMMARY OF THE INVENTION

The present invention provides a method for acylating one or more amino groups of a peptide or protein, the method comprising the steps:
a) reacting the peptide having at least one free amino group with an acylating agent of the general formula I

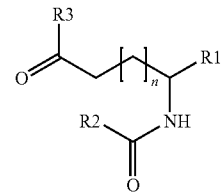

wherein
n is 0-8;
$R^1$ is $COOR^4$;
$R^2$ is a lipophilic moiety;
$R^3$ together with the carboxyl group to which $R^3$ is attached designate a reactive ester or a reactive N-hydroxy imide ester; and
$R^4$ is selected from hydrogen, $C_{1-12}$-alkyl and benzyl,
under basic conditions in an aqueous mixture;
b) if $R^4$ is not hydrogen, saponifying the acylated peptide ester group ($COOR^4$) under basic conditions;
c) isolating the N-acylated peptide,
characterised by said aqueous mixture in step a) containing less than 10% w/w aprotic polar solvent.

In one embodiment of the method, said reaction in step a) takes place in an aqueous mixture containing less than 8% w/w aprotic polar solvent, preferably less than 5% w/w aprotic polar solvent and even more preferable less than 3% w/w aprotic polar solvent.

In another embodiment of the method, the acylating agent is added to the reaction mixture as a solid.

In another embodiment of the method, the acylating agent is added to the reaction mixture as a solution in a aprotic polar solvent which is stabilized by adding an acid.

DESCRIPTION OF THE INVENTION

Peptides and Proteins

The present invention is useful for the introduction of lipophilic acyl groups into any peptide (or protein) in order to reduce the in vivo clearance rate. Examples of such peptides and proteins are ACTH, corticotropin-releasing factor, angiotensin, calcitonin, exendin and analogues thereof, insulin and analogues thereof, glucagon and analogues thereof, glucagon-like peptide-1 and analogues thereof, glucagon-like peptide-2 and analogues thereof, insulin-like growth factor-1, insulin-like growth factor-2, gastric inhibitory peptide, growth hormone-releasing factor, pituitary adenylate cyclase activating peptide, secretin, enterogastrin, somatostatin, somatotropin, somatomedin, parathyroid hormone, thrombopoietin, erythropoietin, hypothalamic releasing factors, prolactin, thyroid stimulating hormones, endorphins, enkephalins, vasopressin, oxytocin, opioids and analogues thereof, superoxide dismutase, interferon, asparaginase, arginase, arginine deaminase, adenosine deaminase and ribonuclease.

It should be understood that the peptide (or protein) should carry at least one free amino group, such an amino group being the N-terminal amino group or a side chain amino group. The peptides or protein may comprise amino acids which are not encoded by the genetic code, such as D-amino acids, 3-hydroxyproline, ornithine and pentylglycine. Particularly interesting are amino groups of lysine and ornithine amino acid residues. The method is particular relevant for the N-acylation of the ∈-amino group of lysine residues. It should also be understood that the peptide or protein in question may comprise two or more pendant amino groups which all may be N-acylated according to the present invention.

The present invention is especially suitable for the acylation of GLP-1 and analogues thereof. Examples of GLP-1 and analogues which can be N-acylated according to the present invention are GLP-1 and truncated analogues, such as $Arg^{26}$-GLP-1(7-37); $Arg^{34}$-GLP-1(7-37); $Lys^{36}$-GLP-1(7-37); $Arg^{26,34}Lys^{36}$-GLP-1(7-37); $Arg^{26,34}Lys^{38}$GLP-1(7-38); $Arg^{26,34}Lys^{39}$-GLP-1(7-39); $Arg^{26,34}Lys^{40}$-GLP-1(7-40); $Arg^{34}Lys^{36}$-GLP-1(7-37); $Arg^{26}Lys^{39}$-GLP-1(7-39); $Arg^{34}Lys^{40}$-GLP-1(7-40); $Arg^{26,34}Lys^{36,39}$-GLP-1(7-39); $Arg^{26,34}Lys^{36,40}$-GLP-1(7-40); $Gly^8Arg^{26}$-GLP-1(7-37); $Gly^8Arg^{34}$-GLP-1(7-37); $Gly^8Lys^{36}$-GLP-1(7-37); $Gly^8Arg^{26,34}Lys^{36}$-GLP-1(7-37); $Gly^8Arg^{26,34}Lys^{39}$-GLP-1(7-39); $Gly^8Arg^{26,34}Lys^{40}$-GLP-1(7-40); $Gly^8Arg^{26}Lys^{36}$-GLP-1(7-37); $Gly^8Arg^{34}Lys^{36}$-GLP-1(7-37); $Lys^{36}$-GLP-1(7-37); $Arg^{26,34}Lys^{36}$-GLP-1(7-37); $Arg^{26,34}$-GLP-1(7-37); $Arg^{26,34}Lys^{40}$-GLP-1(7-37); $Arg^{26}Lys^{36}$-GLP-1(7-37); $Arg^{34}Lys^{36}$-GLP-1(7-37); $Val^8Arg^{22}$-GLP-1(7-37); $Met^8Arg^{22}$-GLP-1(7-37); $Gly^8His^{22}$-GLP-1(7-37); $Val^8His^{22}$-GLP-1(7-37); $Met^8His^{22}$-GLP-1(7-37); $His^{37}$-GLP-1(7-37); $Gly^8$-GLP-1(7-37); $Val^8$-GLP-1(7-37); $Met^8$-GLP-1(7-37); $Gly^8Asp^{22}$-GLP-1(7-37); $Val^8Asp^{22}$-GLP-1(7-37); $Met^8Asp^{22}$-GLP-1(7-37); $Gly^8Glu^{22}$-GLP-1(7-37); $Val^8Glu^{22}$-GLP-1(7-37); $Met^8Glu^{22}$-GLP-1(7-37); $Gly^8Lys^{22}$-GLP-1(7-37); $Val^8Lys^{22}$-GLP-1(7-37); $Met^8Lys^{22}$-GLP-1(7-37); $Gly^8Arg^{22}$-GLP-1(7-37); $Val^8Lys^{22}His^{37}$-GLP-1(7-37); $Gly^8Glu^{22}His^{37}$-GLP-1(7-37); $Val^8Glu^{22}His^{37}$-GLP-1(7-37); $Met^8Glu^{22}His^{37}$-GLP-1(7-37); $Gly^8Lys^{22}His^{37}$-GLP-1(7-37); $Met^8Lys^{22}His^{37}$-GLP-1(7-37); $Gly^8Arg^{22}His^{37}$-GLP-1(7-37); $Val^8Arg^{22}His^{37}$-GLP-1(7-37); $Met^8Arg^{22}His^{37}$-GLP-1(7-37); $Gly^8His^{22}His^{37}$-GLP-1(7-37); $Val^8His^{22}His^{37}$-GLP-1(7-37); $Met^8His^{22}His^{37}$-GLP-1(7-37); $Gly^8His^{37}$-GLP-1(7-37); $Val^8His^{37}$-GLP-1(7-37); $Met^8His^{37}$-GLP-1(7-37); $Gly^8Asp^{22}His^{37}$-GLP-1(7-37); $Val^8Asp^{22}His^{37}$-GLP-1(7-37); $Met^8Asp^{22}His^{37}$-GLP-1(7-37); $Arg^{26}$-GLP-1(7-36)-amide; $Arg^{34}$-GLP-1(7-36)-amide; $Lys^{36}$-GLP-1(7-36)-amide; $Arg^{26,34}Lys^{36}$-GLP-1(7-36)-amide; $Arg^{26,34}$-GLP-1(7-36)-amide; $Arg^{26,34}Lys^{40}$-GLP-1(7-36)-amide; $Arg^{26}Lys^{36}$-GLP-1(7-36)-amide; $Arg^{34}Lys^{36}$-GLP-1(7-36)-amide; $Gly^8$-GLP-1(7-36)-amide; $Val^8$-GLP-1(7-36)-amide; $Met^8$-GLP-1(7-36)-amide; $Gly^8Asp^{22}$-GLP-1(7-36)-amide; $Gly^8Glu^{22}His^{37}$-GLP-1(7-36)-amide; $Val^8Asp^{22}$-GLP-1(7-36)-amide; $Met^8Asp^{22}$-GLP-1(7-36)-amide; $Gly^8Glu^{22}$-GLP-1(7-36)-amide; $Val^8Glu^{22}$-GLP-1(7-36)-amide; $Met^8Glu^{22}$-GLP-1(7-36)-amide; $Gly^8Lys^{22}$-GLP-1(7-36)-amide; $Val^8Lys^{22}$-GLP-1(7-36)-amide; $Met^8Lys^{22}$-GLP-1(7-36)-amide; $Gly^8His^{22}His^{37}$-GLP-1(7-36)-amide; $Gly^8Arg^{22}$-GLP-1(7-36)-amide; $Val^8Arg^{22}$-GLP-1(7-36)-amide; $Met^8Arg^{22}$-GLP-1(7-36)-amide; $Gly^8His^{22}$-GLP-1(7-36)-amide; $Val^8His^{22}$-GLP-1(7-36)-amide; $Met^8His^{22}$-GLP-1(7-36)-amide; $His^{37}$-GLP-1(7-36)-amide; $Val^8Arg^{22}His^{37}$-GLP-1(7-36)-amide; $Met^8Arg^{22}His^{37}$-GLP-1(7-36)-amide; $Gly^8His^{37}$-GLP-1(7-36)-amide; $Val^8His^{37}$-GLP-1(7-36)-amide; $Met^8His^{37}$-GLP-1(7-36)-amide; $Gly^8Asp^{22}His^{37}$-GLP-1(7-36)-amide; $Val^8Asp^{22}His^{37}$-GLP-1(7-36)-amide; $Met^8Asp^{22}His^{37}$-GLP-1(7-36)-amide; $Val^8Glu^{22}His^{37}$-GLP-1(7-36)-amide; $Met^8Glu^{22}His^{37}$-GLP-1(7-36)-amide; $Gly^8Lys^{22}His^{37}$-GLP-1(7-36)-amide; $Val^8Lys^{22}His^{37}$-GLP-1(7-36)-amide; $Met^8Lys^{22}His^{37}$-GLP-1(7-36)-amide; $Gly^8Arg^{22}His^{37}$-GLP-1(7-36)-amide; $Val^8His^{22}His^{37}$-GLP-1(7-36)-amide; $Met^8His^{22}His^{37}$-GLP-1(7-36)-amide; and derivatives thereof.

Each of these GLP-1 analogues and truncated analogues constitutes alternative embodiments of the present invention.

The present invention is also especially suitable for the acylation of GLP-2 and analogues thereof. Examples of GLP-2 and analogues which can be N-acylated according to the present invention are GLP-2 analogues and truncated analogues, such as $Lys^{20}$GLP-2(1-33); $Lys^{20}Arg^{30}$GLP-2(1-33); $Arg^{30}Lys^{34}$GLP-2(1-34); $Arg^{30}Lys^{35}$GLP-2(1-35); $Arg^{30,35}Lys^{20}$GLP-2(1-35); and $Arg^{35}$GLP-2(1-35). Each of these GLP-2 analogues and truncated analogues constitutes alternative embodiments of the present invention.

The present invention is also especially suitable for the acylation of exendin-3 and exendin-4 and analogues thereof. Examples of exendin analogues which can be N-acylated according to the present invention are disclosed in e.g. WO99/43708. Each of these exendin analogues and truncated analogues constitutes alternative embodiments of the present invention.

The present invention is also particularly suited for the acylation of insulin and analogues thereof. Examples of insulin and analogues thereof which can be N-acylated according to the present invention are human insulin and des(B30)-human insulin.

In a further embodiment of the present invention the N-acylation takes place at the ∈-amino group of lysine residues.

Acylating Agent

In the method according to the invention, a peptide (or protein) which has at least one free amino group is reacted with an acylating agent of the general formula I

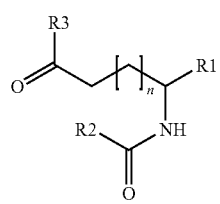

The integer n in formula I is preferably 0-8, in particular 0-6 corresponding, e.g., to aspartic acid, glutamic acid, etc. Preferably, n is 0-4 such as 0-2, e.g. 0 (aspartic acid) or 1 (glutamic acid). Each of these integers and ranges constitutes alternative embodiments of the present invention.

$R^1$ in formula I represents a free acid group (COOH) or an ester group (COOR$^4$). In the cases where $R^1$ is an ester group, $R^4$ is selected from groups which can be removed (as the corresponding alcohols) by hydrolysis under basic conditions. Examples of such groups are $C_{1-12}$-alkyl, e.g. methyl, ethyl, prop-1-yl, prop-2-yl, but-1-yl, but-2-yl, 2-methyl-prop-1-yl, 2-methyl-prop-2-yl(tert-butyl), hex-1-yl, etc., and benzyl. Each of these groups constitutes alternative embodiments of the present invention.

$R^2$ in formula I represents the lipophilic moiety to be incorporated into the peptide or protein. Such a lipophilic moiety is typically selected from $C_{3-39}$-alkyl, $C_{3-39}$-alkenyl, $C_{3-39}$-alkadienyl and steroidal residues. Specific examples of $C_{3-39}$-alkyl are heptyl, nonyl, undecanyl, tridecanyl, pentadecanyl, heptadecanyl, and nonadecanyl. Each of these lipophilic moieties constitutes alternative embodiments of the present invention.

The lipophilic substituent or moiety is characterised by having a solubility in water at 20° C. in the range from about 0.1 mg/100 ml water to about 250 mg/100 ml water, preferable in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml. Each of these lipophilic substituent ranges constitutes alternative embodiments of the present invention.

The terms "$C_{3-39}$-alkyl", "$C_{3-39}$-alkenyl" and "$C_{3-39}$-alkadienyl" is intended to cover straight chain and branched, preferably straight chain, saturated, mono-unsaturated and di-unsaturated, respectively, hydrocarbon radicals of 3-39 carbon atoms. Specific examples of $C_{3-39}$-alkyl are heptyl, nonyl, undecanyl, tridecanyl, pentadecanyl, heptadecanyl, and nonadecanyl.

When used herein, the term "steroidal residue" is intended to mean a lipophilic group which together with the carbonyl group to which $R^2$ is attached is derived from a steroid carboxylic acid, i.e. a tri-, tetra- and pentacyclic, full saturated or partially unsaturated $C_{16-36}$-hydrocarbon. Examples of such groups $R^2$—C(=O)— are lithocholoyl, deoxycholoyl, and choloyl.

Among the lipophilic groups mentioned above, $C_{7-25}$-alkyl, $C_{7-25}$-alkenyl, $C_{7-25}$-alkadienyl and steroidal residues are especially relevant. Particularly interesting examples are heptyl, nonyl, undecanyl, tridecanyl, pentadecanyl, heptadecanyl, nonadecanyl, lithocholoyl, deoxycholoyl, and choloyl. Each of these lipophilic groups constitutes alternative embodiments of the present invention.

$R^3$ in formula I together with the carboxyl group to which $R^3$ is attached designate a reactive ester or a reactive N-hydroxy imide ester. Each of these esters constitutes alternative embodiments of the present invention. Reactive esters and reactive N-hydroxy imide esters are well known in the art of organic chemistry (especially in peptide chemistry) as functional groups which are used in acylation of amino, thio and hydroxy groups. Within the context of the present invention, the term "reactive ester or a reactive N-hydroxy imide ester" is intended to mean an ester functionalised form of a carboxylic acid group suitable for acylating an amine, preferably an primary amine. It should, thus, be understood, that selectivity for acylation of primary amines is preferred over acylating of hydroxy and thio groups. Reactive N-hydroxy imide esters are especially preferred.

Examples of reactive esters are 1-hydroxybenzotriazole esters and derivatives. A number of highly effective reagents, e.g. 2-(1H-benzotriazol-1yl)-1,1,3,3,-tetramethyluronium tetrafluoroborate, for the formation of such activated esters of carboxylic acids are known. Such reactive esters are typically formed in situ in the presence of a base, e.g. an organic base such as an trialkylamine.

Examples of the imide part of reactive N-hydroxy imide esters are those specifically described in EP 0511600 A2, page 3 to page 7. Especially interesting examples of imide parts among those are succinimide, phthalimide, etc. Each of these imide parts constitutes alternative embodiments of the present invention.

The reactive N-hydroxy imide esters of the formula I can be prepared as described in WO00/55119 and WO98/02460.

In the event where the acylating reagent of the formula I is to be used as the free α-carboxylic acid ($R^4$=hydrogen), a compound of the formula I where $R^4$ is a group which can be removed selectively is converted to the corresponding compound where $R^4$ is hydrogen. The carboxylic acid protecting group may be a benzyl group which can be removed by catalytic hydrogenation or an allyl group which can be selectively removed. A benzyl protecting group may be removed by catalytic hydrogenation in an aprotic polar solvent, e.g. in acetone, at room temperature by using palladium-on-carbon and hydrogen. The reaction may be performed in a closed vessel with an hydrogen atmosphere (typically 0.1-10 atm) under vigorous stirring. The reaction is typically completed within 0.5-12 hours depending on the quality of the palladium catalyst. Conventional work-up applies.

Reaction Conditions

The reaction between the acylating agent of the formula I and the peptide or protein is performed under basic conditions in an aqueous solution containing less than 10% w/w of an aprotic polar solvent.

In one embodiment of the invention the reaction in step a) is performed in an aqueous solution containing from 0% w/w to 10% w/w of an aprotic polar solvent.

In another embodiment of the invention the reaction in step a) is performed in an aqueous solution containing from 1% w/w to 10% w/w of an aprotic polar solvent.

In another embodiment of the invention the reaction in step a) is performed in an aqueous solution containing from 1% w/w to 8% w/w of an aprotic polar solvent.

The acylating agent of the formula I is typically used in a slight excess relative to the number of amino groups of the peptide to be acylated. The ratio is typically 1:1 to 1:20 with an excess of the acylating agent, preferably 1:1.2 to 1:5, taking into account the number of amino groups in the peptide. The acylating agent may be added to the reaction mixture as a solid or it may be added to the reaction mixture as a solution. When the acylating agent is added as a solution it is dissolved in an aprotic polar solvent and preferably stabilized by adding an acid. Typically, the acid for the stabilization is a mineral acid, e.g. sulfuric acid.

It should be understood that the peptide may be fully N-acylated or only partially N-acylated depending on the amount of acylating agent used and the reaction conditions. It is preferred that the N-acylation is substantially stoichiometrical.

Aprotic polar solvents are solvents with moderately high dielectric constants which do not contain acidic hydrogen (see e.g. Morrison and Boyd, Organic Chemistry, $5^{th}$ ed. p 229). Typically, the aprotic polar solvent is selected from anhydrous tetrahydrofuran (THF), anhydrous dimethylformamide (DMF), acetone, dichloromethane, dimethylsulfoxide (DMSO), dioxane, dimethylacetamide, and N-methyl-2-pyrrolidone and mixtures thereof, among which dimethylformamide, dimethylsulfoxide, dimethylacetamide and N-methyl-2-pyrrolidone are preferred and N-methyl-2-pyrrolidone is especially preferred.

The temperature is typically kept in the range of −10-50° C.

It is important that the pH value of the solvent mixture is in the range of 7-14, such as 9-13, preferably in the range of 10-12, in order for the reaction to proceed smoothly. The result with respect to yield and purity is normally optimal when the pH value of the solvent mixture is in the range of 10-12. The desired pH value is obtained by addition of alkalimetal hydroxides, e.g. sodium hydroxide and potassium hydroxide, and/or organic bases such as trialkylamines (e.g. triethylamine, N,N-diisopropylethylamine, etc.). It may also be advantageous to add a buffer which is suitable for keeping the pH near the starting value before the reaction starts. Examples of buffer which may be used for this purpose is phosphate buffer, borate buffer and the like.

As a typical example, the reaction in step (a) is performed using the protein and the acylating agent of the formula I in a 1:1 to 1:5 molar ratio. The peptide is typically predissolved in water at −10-30° C. such as 0-25° C. and the pH is adjusted to the desired level using a alkalimetal hydroxide (e.g. sodium hydroxide or potassium hydroxide). The pH value may be further adjusted using acids, e.g. acetic acid, and bases, e.g. trialkylamine, but the temperature is preferably within the above range. Alternatively the peptide is pre-dissolved directly in an aqueous solution of an appropriate amount of the relevant acid or base. The acylating agent is subsequently added as a solid or as a solution in an aprotic polar solvent. The reaction is typically allowed to proceed to completion (can be monitored by HPLC) which is typically obtained within 0.2-4 hours, such as 0.2-1 hour, before addition of water and an acid, e.g. acetic acid, to pH 6.5-9.0. The product is typically isolated and purified by HPLC, or is precipitated by isoelectric pH, or is hydrolysed (step (b)) before purification.

When an acylating agent of the formula I where $R^4$ is hydrogen is used, the N-acylated peptide or protein carrying lipophilic moieties and free carboxylic groups is obtained directly. Thus, the variant where $R^4$ is hydrogen represents a preferred embodiment of the method of the present invention.

Alternatively, i.e. when the group $R^4$ is $C_{1-12}$-alkyl or benzyl, the N-acylated peptide ester (or protein ester) is saponified under basic conditions so as to obtain the N-acylated peptide or N-acylated protein. Saponification is typically performed in a 0.01-4.0 M solution of an alkalimetal hydroxide, e.g. sodium or potassium hydroxide. The pH of the solution is typically 10-14. The reaction is typically allowed to proceed for 0.1-12 hours, preferably for 0.5-4 hours, at 0-40° C. such as around room temperature. After reaction, the product is purified, e.g. by precipitation at isoelectric pH and/or by preparative HPLC. Thus, the variant where $R^4$ is $C_{1-12}$-alkyl or benzyl represents another preferred embodiment of the method of the present invention.

In one embodiment of the method, the acylating agent is added to the reaction mixture as a solid.

In another embodiment of the method, said reaction in step a) takes place in an aqueous mixture containing from 0% w/w to 8% w/w aprotic polar solvent, preferably from 0% w/w to 5% w/w aprotic polar solvent and even more preferable from 0% w/w to 3% w/w aprotic polar solvent.

In yet another embodiment of the method, said reaction in step a) takes place in the presence of an aprotic polar solvent, and said aprotic polar solvent is selected from the group consisting of N-methyl-2-pyrrolidone, tetrahydrofurane and dimethylsulfoxide.

In yet another embodiment of the method, all of the aprotic organic solvent is added to the reaction mixture as a solvent for the acylating agent.

In yet another embodiment of the method, the acylating agent is added to the reaction mixture as a solution which is stabilized by adding an acid.

In yet another embodiment of the method, said acid is added to the aprotic polar solvent in a concentration from 0.01% w/w to 1% w/w, preferably in a concentration from 0.05% w/w to 0.5% w/w.

In yet another embodiment of the method, said acid is selected from the group consisting of sulphuric acid, methanesulphonic acid and trifluoroacetic acid.

In yet another embodiment of the method, the reaction in step a) takes place in the absence of an aprotic polar solvent.

In yet another embodiment of the method, $R^4$ in formula I is hydrogen.

In yet another embodiment of the method, $R^4$ is selected from $C_{1-8}$-alkyl and benzyl.

In yet another embodiment of the method, $R^3$ together with the carboxyl group to which $R^3$ is attached designate a reactive N-hydroxy imide ester.

In yet another embodiment of the method, the acylated peptide ester is saponified at a pH value in the range of 10-14, preferably in the pH range from 9-13.

In yet another embodiment of the method, the acylated peptide ester is saponified at a pH value in the range of 9-14, such as in the pH range from 10-13.

In yet another embodiment of the method, pH of the reaction mixture in step a) is from pH 9 to pH 13, preferably from pH 10 to pH 12, or more preferable from pH 11.0 to pH 11.5.

In yet another embodiment of the method, the reaction mixture in step a) comprises a buffer which is suitable for maintaining a substantially constant pH during the reaction. In one embodiment of the method said buffer is a phosphate buffer, a borate buffer or a mixture thereof.

In yet another embodiment of the method, the temperature of the reaction mixture in step a) is in the range of 0-50° C., preferably in the range from 5-40° C. and more preferable in the range from 10-30° C.

In yet another embodiment of the method, $R^2$ is selected from $C_{3-39}$-alkyl, $C_{3-39}$-alkenyl, $C_{3-39}$-alkadienyl and steroidal residues.

In yet another embodiment of the method, $R^2$—C(=O)— is selected from the group consisting of lithocholoyl and hexadecanoyl.

In yet another embodiment of the method, said peptide used as starting material for step a) has a peptide purity of at least 80%, at least 90%, at least 93%, at least 95%, or at least 97% as determined by RP-HPLC.

In yet another embodiment of the method, said peptide is selected from the group consisting of GLP-1, exendin-4, GLP-2, glucagon, insulin, analogues thereof and derivatives of any of the foregoing.

In yet another embodiment of the method, said peptide is a GLP-1 agonist.

In yet another embodiment of the method, said peptide is selected from the group consisting of exendin-3, exendin-4, Arg$^{34}$-GLP-1(7-37), Gly$^8$-GLP-1(7-36)-amide, Gly$^8$-GLP-1(7-37), Val$^8$-GLP-1(7-36)-amide, Val$^8$-GLP-1(7-37), Val$^8$Asp$^{22}$-GLP-1(7-36)-amide, Val$^8$Asp$^{22}$-GLP-1(7-37), Val$^8$Glu$^{22}$-GLP-1(7-36)-amide, Val$^8$Glu$^{22}$-GLP-1(7-37), Val$^8$Lys$^{22}$-GLP-1(7-36)-amide, Val$^8$Lys$^{22}$-GLP-1(7-37), Val$^8$Arg$^{22}$-GLP-1(7-36)-amide, Val$^8$Arg$^{22}$-GLP-1(7-37), Val$^8$His$^{22}$-GLP-1(7-36)-amide, Val$^8$His$^{22}$-GLP-1(7-37), des (B30) human insulin and derivatives thereof.

In yet another embodiment of the method, said peptide is selected from the group consisting of consisting of Val$^8$Trp$^{19}$Glu$^{22}$-GLP-1(7-37), Val$^8$Glu$^{22}$Val$^{25}$-GLP-1(7-37), Val$^8$Tyr$^{16}$Glu$^{22}$-GLP-1(7-37), Val$^8$Trp$^{16}$Glu$^{22}$-GLP-1(7-37), Val$^8$Leu$^{16}$Glu$^{22}$-GLP-1(7-37), Val$^8$Tyr$^{18}$Glu$^{22}$-GLP-1(7-37), Val$^8$Glu$^{22}$His$^{37}$-GLP-1(7-37), Val$^8$Glu$^{22}$Ile$^{33}$-GLP-1(7-37), Val$^8$Trp$^{16}$Glu$^{22}$Val$^{25}$Ile$^{33}$-GLP-1(7-37), Val$^8$Trp$^{16}$Glu$^{22}$Ile$^{33}$-GLP-1(7-37), Val$^8$Glu$^{22}$Val$^{25}$Ile$^{33}$-GLP-1(7-37), Val$^8$Trp$^{16}$Glu$^{22}$Val$^{25}$-GLP-1(7-37) and analogues thereof.

In yet another embodiment of the method, said peptide is selected from HGEGTFTSDLSKQMEEEAVR-LFIEWLKNGGPSSGAPPSKKKKKK-NH2 (ZP-10) and analogues thereof.

In another embodiment of the method, said peptide is not an insulin peptide, i.e. it is not insulin or an analogue thereof. In yet another embodiment of the method, said peptide comprises only one polypeptide chains. In yet another embodiment of the method, said peptide comprises two polypeptide chains which are covalently connected by at least one disulfide bond.

Another aspect of the present invention is the use of the acylation method for the preparation of a peptide derivative selected from the group consisting of Arg$^{34}$, Lys$^{26}$(N$^\in$-(γ-Glu(N$^\alpha$-hexadecanoyl)))-GLP-1(7-37) and Lys$^{B29}$(N$^\in$-tetradecanoyl) des(B30) human insulin and Lys$^{B29}$(N$^\in$[N$^\alpha$-lithocholoyl-Glu-OH]) des(B30) human insulin.

EXAMPLES

Preparation of the acylation reagents is done as described in WO 00/55119.

In the examples final purification of the product was obtained by column chromatography.

Example 1

Arg$^{34}$GLP-1$_{(7-37)}$ was expressed in yeast (*S. cerevisiae*) by conventional recombinant DNA technology, e.g. as described in WO 98/08871. Arg$^{34}$GLP-1$_{(7-37)}$ in the fermentation broth was then purified by conventional reversed phase chromatography and subsequently precipitated at the isoelectric pH of the peptide, i.e. at pH 5.4. The precipitate was isolated by centrifugation and frozen.

Arg$^{34}$-GLP-1$^{7-37}$ (1.47 g of frozen iso-precipitated peptide material, approx. 0.10 mmol) was dissolved in 0.1 mol/kg triethylamine (23 ml) at 10-15° C. The pH of the solution was 11.6. N-hexadecanoylglutamic acid γ-N-hydroxysuccinimide ester (63.7 mg, 0.13 mmol) was added.

After 20 minutes at room temperature water (42 ml) was added, and the pH was adjusted to 8.0 by addition of 1.0 M acetic acid.

Yield: By analytical RP-HPLC the reaction mixture was shown to contain 84% (by area) of Arg$^{34}$Lys$^{26}$-[N-$\in$-(γ-Glu(N-hexadecanoyl))]-GLP-1$^{7-37}$ and 0.5% (by area) of Arg$^{34}$Lys$^{26}$-[N-$\in$-(α-Glu(N-hexadecanoyl))]-GLP-1$^{7-37}$.

Example 2

Arg$^{34}$GLP-1$_{(7-37)}$ was expressed in yeast (*S. cerevisiae*) by conventional recombinant DNA technology, e.g. as described in WO 98/08871. Arg$^{34}$GLP-1$_{(7-37)}$ in the fermentation broth was then purified by conventional reversed phase chromatography and subsequently precipitated at the isoelectric pH of the peptide, i.e. at pH 5.4. The precipitate was isolated by centrifugation and frozen.

Arg$^{34}$-GLP-1$^{7-37}$ (1.57 g of frozen iso-precipitated peptide material, approx. 0.14 mmol) was dissolved in 0.1 mol/kg triethylamine (23 ml) at 10-15° C. The pH of the solution was adjusted to 11.5 by the addition of triethylamine. 1.7 mL of N-hexadecanoylglutamic acid γ-N-hydroxysuccinimide ester (92.1 mg, 0.19 mmol) dissolved in N-methyl-2-pyrrolidone containing 0.105% w/w 1 M H2SO4 was added. After 20 minutes at room temperature water (42 ml) was added, and the pH was adjusted to 8.0 by addition of 1.0 M acetic acid.

Yield: By analytical RP-HPLC the reaction mixture was shown to contain 83% (by area) of Arg$^{34}$Lys$^{26}$-[N-$\in$-(γ-Glu(N-hexadecanoyl))]-GLP-1$^{7-37}$ and 0.4% (by area) of Arg$^{34}$Lys$^{26}$-[N-$\in$-(α-Glu(N-hexadecanoyl))]-GLP-1$^{7-37}$.

Example 3

Arg$^{34}$GLP-1$_{(7-37)}$ was expressed in yeast (*S. cerevisiae*) by conventional recombinant DNA technology, e.g. as described in WO 98/08871. Arg$^{34}$GLP-1$_{(7-37)}$ in the fermentation broth was then purified by conventional reversed phase chromatography and subsequently precipitated at the isoelectric pH of the peptide, i.e. at pH 5.4. The precipitate was isolated by centrifugation and frozen.

Arg$^{34}$-GLP-1$^{7-37}$ (1.53 g of frozen iso-precipitated peptide material, approx. 0.13 mmol) was dissolved in 0.05 mol/kg triethylamine (25 ml) at room temperature. The pH of the solution was 10.9. 1.8 ml of N-hexadecanoylglutamic acid γ-N-hydroxysuccinimide ester (94.2 mg, 0.19 mmol) dissolved in N-methyl-2-pyrrolidone without H$_2$SO$_4$ was added. After 30 minutes at room temperature water (48 ml) was added, and the pH was adjusted to 8.0 by addition of 1.0 M acetic acid.

Yield: By analytical RP-HPLC the reaction mixture was shown to contain 75% (by area) of Arg$^{34}$Lys$^{26}$-[N-$\in$-(γ-Glu(N-hexadecanoyl))]-GLP-1$^{7-37}$ and 4.0% (by area) of Arg$^{34}$Lys$^{26}$-[N-$\in$-(α-Glu(N-hexadecanoyl))]-GLP-1$^{7-37}$.

Example 4

Reference Example with Aprotic Polar Solvent Conc.>10 w/w

Arg$^{34}$GLP-1$_{(7-37)}$ was expressed in yeast (*S. cerevisiae*) by conventional recombinant DNA technology, e.g. as described in WO 98/08871. Arg$^{34}$GLP-1$_{(7-37)}$ in the fermentation broth was then purified by conventional reversed phase chromatography and subsequently precipitated at the isoelectric pH of the peptide, i.e. at pH 5.4. The precipitate was isolated by centrifugation and frozen.

Arg$^{34}$-GLP-1$^{7-37}$ (1.57 g of frozen iso-precipitated peptide material, approx. 0.14 mmol) was dissolved in 0.1 mol/kg triethylamine (23 ml) at 10-15° C. N-methyl-2-pyrrolidone (6.8 ml) was added and the pH of the solution was adjusted to 11.5 by the addition of triethylamine. Then N-hexadecanoylglutamic acid γ-N-hydroxysuccinimide ester (92.1 mg, 0.19 mmol) dissolved in 1.7 ml N-methyl-2-pyrrolidone containing 0.105% w/w 1M H$_2$SO$_4$ was added. After 20 minutes at room temperature water (54 ml) was added, and the pH was adjusted to 8.0 by addition of 1.0 M acetic acid.

Yield: By analytical RP-HPLC the reaction mixture was shown to contain 87% (by area) of Arg$^{34}$Lys$^{26}$-[N-∈-(γ-Glu(N-hexadecanoyl))]-GLP-1$^{7-37}$ and 0.5% (by area) of Arg$^{34}$Lys$^{26}$-[N-∈-(α-Glu(N-hexadecanoyl))]-GLP-1$^{7-37}$.

Example 5

Reference Example with Aprotic Polar Solvent Conc.>10 w/w

Arg$^{34}$GLP-1$_{(7-37)}$ was expressed in yeast (*S. cerevisiae*) by conventional recombinant DNA technology, e.g. as described in WO 98/08871. Arg$^{34}$GLP-1$_{(7-37)}$ in the fermentation broth was then purified by conventional reversed phase chromatography and subsequently precipitated at the isoelectric pH of the peptide, i.e. at pH 5.4. The precipitate was isolated by centrifugation and frozen.

Arg$^{34}$-GLP-1$^{7-37}$ (1.51 g of frozen iso-precipitated peptide material, approx. 0.13 mmol) was dissolved in 0.1 mol/kg triethylamine (20 ml) and N-methyl-2-pyrrolidone (100 ml) at 10-15° C. Then N-hexadecanoylglutamic acid γ-N-hydroxysuccinimide ester (74 mg, 0.15 mmol) dissolved in 1.4 ml N-methyl-2-pyrrolidone containing 0.105% w/w 1M H$_2$SO$_4$ was added. After 45 minutes at room temperature water (206 ml) was added, and the pH was adjusted to 8 by addition of 1.0 M acetic acid.

Yield: By analytical RP-HPLC the reaction mixture was shown to contain 57% (by area) of Arg$^{34}$Lys$^{26}$-[N-∈-(γ-Glu(N-hexadecanoyl))]-GLP-1$^{7-37}$ and 14% (by area) of Arg$^{34}$Lys$^{26}$-[N-∈-(α-Glu(N-hexadecanoyl))]-GLP-1$^{7-37}$.

Example 6

In table 1 the experimental conditions used for acylating Arg$^{34}$-GLP-1$^{7-37}$ in the experiments of example 1-5 are summarised and the resulting contents of the impurity Arg$^{34}$Lys$^{26}$-[N-∈-(α-Glu(N-hexadecanoyl))]-GLP-1$^{7-37}$ (abbreviated α-glu) are listed. Without the addition of H$_2$SO$_4$ as stabilizer it is clear that lower concentrations of aprotic polar solvent is effective in reducing the amount of the α-glu impurity. When the stabilizer is added the formation of significant amounts of the α-glu impurity start at significantly higher concentrations of aprotic polar solvent, i.e. above the concentration 28% w/w.

TABLE 1

The contents of aprotic polar solvent in the reaction mixture when acylating GLP-1 peptides and the resulting fraction of the impurity Arg$^{34}$Lys$^{26}$-[N-ε-(α-Glu(N-hexadecanoyl))]-GLP-1$^{7-37}$ (α-glu).

| Example # | Aqueous peptide solution (mL) | NMP added (mL) | NMP contents (% w/w) | H$_2$SO$_4$ added | α-glu |
|---|---|---|---|---|---|
| 1 | 23 | 0 | 0% | – | 0.5% |
| 2 | 23 | 1.7 | 7% | + | 0.4% |

TABLE 1-continued

The contents of aprotic polar solvent in the reaction mixture when acylating GLP-1 peptides and the resulting fraction of the impurity Arg$^{34}$Lys$^{26}$-[N-ε-(α-Glu(N-hexadecanoyl))]-GLP-1$^{7-37}$ (α-glu).

| Example # | Aqueous peptide solution (mL) | NMP added (mL) | NMP contents (% w/w) | H$_2$SO$_4$ added | α-glu |
|---|---|---|---|---|---|
| 3 | 25 | 1.8 | 7% | – | 4% |
| 4 | 23 | 6.8 + 1.7 | 28% | + | 0.5% |
| 5 | 20 | 100 + 1.4 | 84% | + | 14% |

(Data from Examples 1-5).

Example 7

Sodium-crystallized des(B30)-human insulin (1.74 g of frozen peptide material isolated by isoelectric precipitation, approx. 0.088 mmol) was dissolved in 0.1 mol/kg triethylamine (10.85 ml) at room temperature. The pH of the solution was 10.9. Then, methyl (2S)-5-[(2,5-dioxo-1-pyrrolidinyl)oxy]-2-{[(3a,5b)-3-hydroxy-9-methyl-24-oxo-cholan-24-yl]amino}-5-oxopentanoate (55.1 mg, 0.089 mmol) dissolved in N-methyl-2-pyrrolidone (1.25 ml) was added. After 30 minutes at room temperature water (5° C., 85 ml) was added.

Yield: By analytical RP-HPLC the reaction mixture was shown to contain 34% (by area) of N∈-(lithocholoyl-γ-glutamyl)-Lys$^{B29}$-des(B30)-human insulin.

Example 8

Arg$^{34}$GLP-1$_{(7-37)}$ was expressed in yeast (*S. cerevisiae*) by conventional recombinant DNA technology, e.g. as described in WO 98/08871. Arg$^{34}$GLP-1$_{(7-37)}$ in the fermentation broth was then purified by conventional reversed phase chromatography and subsequently precipitated at the isoelectric pH of the peptide, i.e. at pH 5.4. The precipitate was isolated by centrifugation and frozen.

The isoelectric precipitate containing Arg$^{34}$GLP-1$_{(7-37)}$ (5.70 g of frozen precipitated peptide material, approx. 0.38 mmol) was dissolved in 0.1 M disodiumhydrogenphosphate dihydrate solution (170 mL, pH adjusted to 11.35 with 1 M NaOH) at 15° C. The pH of the solution was re-adjusted to 11.4 by the addition of 1 M NaOH. 3 mL of N-hexadecanoylglutamic acid γ-N-hydroxysuccinimide ester (248.1 mg, 0.51 mmol) dissolved in N-methyl-pyrrolidone containing 0.105% w/w 1 M H$_2$SO$_4$ was added dropwise during 8 min.

Samples were drawn out during 21.5 hours of reaction at 15° C. and added 0.1 M sodiumdihydrogenphosphate dihydrate solution containing 1 mg/mL glycine, pH 7.5. The final reaction mixture was diluted with water (300 mL) and the pH was adjusted to 8.0 by addition of glacial acid.

Yield: By analytical RP-HPLC the reaction mixture was shown to contain 78-80% (by area) of Arg$^{34}$Lys$^{26}$-[N-∈-(γ-Glu(N-hexadecanoyl))]-GLP-1$^{7-37}$ and 0.24-1.67% (by area) of Arg$^{34}$Lys$^{26}$-[N-∈-(α-Glu(N-hexadecanoyl))]-GLP-1$^{7-37}$.

TABLE 2

The content of Arg$^{34}$Lys$^{26}$-[N-ε-(γ-Glu(N-hexadecanoyl))]-GLP-1$^{7-37}$ (γ-Glu) and Arg$^{34}$Lys$^{26}$-[N-ε-(α-Glu(N-hexadecanoyl))]-GLP-1$^{7-37}$ (α-Glu) vs. time of reaction.

| Time (hrs) | γ-Glu (% by area) | α-Glu (% by area) |
|---|---|---|
| 0.17 | 78.01 | 0.24 |
| 1 | 79.35 | 0.31 |
| 2 | 79.45 | 0.36 |
| 4 | 80.49 | 0.45 |
| 21.5 | 80.27 | 1.67 |

(Data from Example 8).

The invention claimed is:

1. A method for producing an N-acylated peptide, said method comprising:

a) reacting a peptide having at least one free amino group with an acylating agent of the general formula I

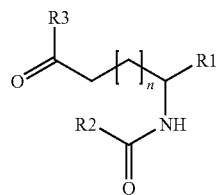

wherein
n is 0-8;
$R^1$ is $COOR^4$;
$R^2$ is selected from $C_{3-39}$-alkyl, $C_{3-39}$-alkenyl, $C_{3-39}$-alkadienyl and steroidal residues;
$R^3$ together with the carboxyl group to which $R^3$ is attached designate a reactive ester or a reactive N-hydroxy imide ester; and
$R^4$ is selected from hydrogen;
wherein said peptide is $Arg^{34}Lys^{26}(N^{\in}$-(γ-Glu($N^{\alpha}$-hexadecanoyl)))-GLP-1(7-37);
wherein the acylating agent is in an aqueous mixture under basic conditions containing 7% w/w or less aprotic polar solvent stabilized with an acid; and wherein said N-acylated peptide contains no more than 2% of the closely-related impurity $Arg^{34}Lys^{26}$-[N-∈-(α-Glu(N-hexadecanoyl))]-GLP-$1^{7-37}$ as determined by RP-HPLC.

2. The method according to claim 1, wherein said reaction in step a) takes place in an aqueous mixture containing less than 5% w/w aprotic polar solvent.

3. The method according to claim 1, wherein said reaction in step a) takes place in an aqueous mixture containing less than 3% w/w aprotic polar solvent.

4. The method according to claim 1, wherein the acylating agent is added to the reaction mixture in step a) as a solid.

5. The method according to claim 1, wherein said aprotic polar solvent is selected from the group consisting of N-methyl-2-pyrrolidone, tetrahydrofurane and dimethyl sulfoxide.

6. The method according to claim 1, wherein all of the aprotic polar solvent is added to the reaction mixture as a solvent for the acylating agent.

7. The method according to claim 1, wherein said acid is added to the aprotic polar solvent in a concentration from 0.01% w/w to 1% w/w.

8. The method according to claim 1, wherein said acid is added to the aprotic polar solvent in a concentration from 0.05% w/w to 0.5% w/w.

9. The method according to claim 1, wherein said acid is selected from the group consisting of sulphuric acid, methanesulphonic acid and trifluoroacetic acid.

10. The method according to claim 1, wherein the reaction in step a) takes place in the absence of an aprotic polar solvent.

11. The method according to claim 1, wherein $R^3$ together with the carboxyl group to which $R^3$ is attached designate a reactive N-hydroxy imide ester.

12. The method according to claim 1, wherein pH of the reaction mixture in step a) is from pH 9 to pH 13.

13. The method according to claim 1, wherein pH of the reaction mixture in step a) is from pH 10 to pH 12.

14. The method according to claim 1, wherein pH of the reaction mixture in step a) is from pH 11.0 to pH 11.5.

15. The method according to claim 1, wherein the temperature of the reaction mixture in step a) is in the range of 0-50° C.

16. The method according to claim 1, wherein the temperature of the reaction mixture in step a) is in the range from 5-40° C.

17. The method according to claim 1, wherein the temperature of the reaction mixture in step a) is in the range from 10-30° C.

18. The method according to claim 1, wherein $R^2$—C(=O)— is selected from the group consisting of lithocholoyl and hexadecanoyl.

19. The method according to claim 1, wherein said peptide used as starting material for step a) has a peptide purity of at least 80 as determined by RP-HPLC.

20. The method according to claim 1, wherein said peptide used as starting material for step a) has a peptide purity of at least 90% as determined by RP-HPLC.

21. The method according to claim 1, wherein said peptide used as starting material for step a) has a peptide purity of at least 93% as determined by RP-HPLC.

22. The method according to claim 1, wherein said peptide used as starting material for step a) has a peptide purity of at least 95% as determined by RP-HPLC.

23. The method according to claim 1, wherein said peptide used as starting material for step a) has a peptide purity of at least 97% as determined by RP-HPLC.

24. The method according to claim 1, wherein said peptide is selected from HGEGTFTSDLSKQMEEEAVR-LFIEWLKNGGPSSGAPPSKKKKKK-NH2 (ZP-10) and analogues thereof.

25. The method according to claim 1, wherein the reaction mixture in step a) comprises a buffer which is suitable for maintaining a substantially constant pH during the reaction.

* * * * *

SEQUENCE LISTING

```
<160> NUMBER OF SEQ ID NOS: 10

<210> SEQ ID NO 1
<211> LENGTH: 34
<212> TYPE: PRT
<213> ORGANISM: Artificial Sequence
<220> FEATURE:
<223> OTHER INFORMATION: Synthetic

<400> SEQUENCE: 1

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Lys Asp

<210> SEQ ID NO 2
<211> LENGTH: 34
<212> TYPE: PRT
<213> ORGANISM: Artificial Sequence
<220> FEATURE:
<223> OTHER INFORMATION: Synthetic

<400> SEQUENCE: 2

His Ala Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Arg Lys

<210> SEQ ID NO 3
<211> LENGTH: 34
<212> TYPE: PRT
<213> ORGANISM: Artificial Sequence
<220> FEATURE:
<223> OTHER INFORMATION: Synthetic

<400> SEQUENCE: 3

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Arg Asp

<210> SEQ ID NO 4
<211> LENGTH: 34
<212> TYPE: PRT
<213> ORGANISM: Artificial Sequence
<220> FEATURE:
<223> OTHER INFORMATION: Synthetic
```

<400> SEQUENCE: 4

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Lys Asp

<210> SEQ ID NO 5
<211> LENGTH: 34
<212> TYPE: PRT
<213> ORGANISM: Artificial Sequence
<220> FEATURE:
<223> OTHER INFORMATION: Synthetic

<400> SEQUENCE: 5

His Gly Glu Gly Thr Phe Thr Ser Asp Val Ser Ser Tyr Leu Glu Gly
1               5                   10                  15

Gln Ala Ala Arg Glu Phe Ile Ala Trp Leu Val Arg Gly Lys Gly Arg
            20                  25                  30

Arg Lys

<210> SEQ ID NO 6
<211> LENGTH: 34
<212> TYPE: PRT
<213> ORGANISM: Artificial Sequence
<220> FEATURE:
<223> OTHER INFORMATION: Synthetic

<400> SEQUENCE: 6

His Val Glu Gly Thr Phe Thr Ser Asp Trp Ser Ser Tyr Leu Glu Glu
1               5                   10                  15

Gln Ala Val Lys Glu Phe Ile Ala Trp Leu Ile Lys Gly Arg Gly Arg
            20                  25                  30

Arg Asp

<210> SEQ ID NO 7
<211> LENGTH: 34
<212> TYPE: PRT
<213> ORGANISM: Artificial Sequence
<220> FEATURE:
<223> OTHER INFORMATION: Synthetic

<400> SEQUENCE: 7

His Val Glu Gly Thr Phe Thr Ser Asp Trp Ser Ser Tyr Leu Glu Glu
1               5                   10                  15

Gln Ala Ala Lys Glu Phe Ile Ala Trp Leu Ile Lys Gly Arg Gly Arg
            20                  25                  30

Arg Asp

<210> SEQ ID NO 8
<211> LENGTH: 34
<212> TYPE: PRT
<213> ORGANISM: Artificial Sequence
<220> FEATURE:
<223> OTHER INFORMATION: Synthetic

<400> SEQUENCE: 8

His Val Glu Gly Thr Phe Thr Ser Asp Val Ser Ser Tyr Leu Glu Glu
1               5                   10                  15

Gln Ala Val Lys Glu Phe Ile Ala Trp Leu Ile Lys Gly Arg Gly Arg

```
                    20                  25                  30
Arg Asp

<210> SEQ ID NO 9
<211> LENGTH: 34
<212> TYPE: PRT
<213> ORGANISM: Artificial Sequence
<220> FEATURE:
<223> OTHER INFORMATION: Synthetic

<400> SEQUENCE: 9

His Val Glu Gly Thr Phe Thr Ser Asp Trp Ser Ser Tyr Leu Glu Glu
1               5                   10                  15

Gln Ala Val Lys Glu Phe Ile Ala Trp Leu Val Lys Gly Arg Gly Arg
                20                  25                  30

Arg Asp

<210> SEQ ID NO 10
<211> LENGTH: 44
<212> TYPE: PRT
<213> ORGANISM: Artificial Sequence
<220> FEATURE:
<223> OTHER INFORMATION: Synthetic

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Lys
                35                  40
```